(12) United States Patent
Tanaka et al.

(10) Patent No.: US 9,353,364 B2
(45) Date of Patent: *May 31, 2016

(54) β-GLUCOSIDASE

(71) Applicant: HONDA MOTOR CO., LTD., Minato-Ku, Tokyo (JP)

(72) Inventors: Maiko Tanaka, Wako (JP); Shigenobu Mitsuzawa, Wako (JP); Satoru Shinkawa, Wako (JP); Daisuke Shibata, Kisarazu (JP); Takeshi Ara, Kisarazu (JP); Migiwa Takeda, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 34 days.

This patent is subject to a terminal disclaimer.

(21) Appl. No.: 14/324,281

(22) Filed: Jul. 7, 2014

(65) Prior Publication Data

US 2015/0017690 A1 Jan. 15, 2015

(30) Foreign Application Priority Data

Jul. 9, 2013 (JP) .................................. 2013-143259

(51) Int. Cl.
*C12N 9/24* (2006.01)
*C12N 9/42* (2006.01)
*C12P 19/14* (2006.01)
*D21C 5/00* (2006.01)
*C12P 19/02* (2006.01)

(52) U.S. Cl.
CPC ............... *C12N 9/2445* (2013.01); *C12P 19/02* (2013.01); *C12P 19/14* (2013.01); *C12Y 302/01021* (2013.01); *D21C 5/005* (2013.01); *Y02P 20/52* (2015.11)

(58) Field of Classification Search
CPC .................................................. C12N 9/2402
See application file for complete search history.

(56) References Cited

U.S. PATENT DOCUMENTS

| 8,772,010 B2 | 7/2014 | Zhang et al. |
| 2004/0091469 A1 | 5/2004 | Fukasawa et al. |

FOREIGN PATENT DOCUMENTS

| EP | 2 468 859 A1 | 6/2012 |
| EP | 2 554 667 A1 | 2/2013 |
| JP | 2001-017180 A | 1/2001 |
| JP | 2010-148427 A | 7/2010 |
| WO | 2013/091544 A1 | 6/2013 |

OTHER PUBLICATIONS

Extended European search report, mailing date of Jan. 5, 2015, issued in EP Patent Application 14175790.6.
Extended European search report, mailing date of Jan. 5, 2015, issued in EP Patent Application 14175787.2.
Database UniProt [Online]Dec. 16, 2008, "SubName: Full=Beta-glucosidase 1, putatiive {ECO:00003131 EMBL:EEA28836.1 };", XP002733567, retrieved from EBI accession No. UNIPROT:B6Q884 Database accession No. B6Q884 *the whole document*.
Database EMBL [Online] Jan. 2, 2000, "Coccidioides immitis beta-glucosidase precursor (bgl2) gene, complete cds." XP002733568, retrieved from EBI accession No. EM STD: AF022893 Database accession No. AF022893 *the whole document *.
Database UniProt [Online] Dec. 16, 2008, "SubName: Full=Beta-glucosidase, putative {ECO: 00003131 EMBL: EEA I9214.I};", XP002733544, retrieved from EBI accession No. UNIPROT:B6QW86 Database accession No. B6QW86 * the whole document *.
extended EP Search Report with a mailing date of Nov. 7, 2014 in EP Patent Application 14175786.4.
Extended EP Search Report with a mailing date of Nov. 7, 2014 in EP Patent Application 14175789.8.
Prasetyo, Joni et al., "Response of Cellulase Activity in pH-controlled cultures of the filamentous fungus Acremonium cellulolyticus", Applied Biochemistry and Biotechnology, Humana Press, Inc. US, vol. 162, No. 1, Sep. 1, 2010, pp. 52-61.
Fujii, Tatsuya et al., "Enzymatic hydrolyzing performance of Acremonium cellulolyticus and Trichoderma reesei against three lignocellulosic materials", Biotechnology for Biofuels, Biomed Central Ltd, GB, vol. 2, No. 1, Oct. 1, 2009, p. 24.
Database UniProt [Online] Mar. 3, 2009, "SubName: Full=Beta-glucosidase {ECO: 0000313:EMBL:EED14314.1};".
Database UniProt [Online] Dec. 16, 2008, "SubName:Full=Beta-glucosidase {ECO: 0000313:EMBL: EEA19886.1};".
Database UniProt [Online} Mar. 3, 2009, "SubName: Full=Beta-glucosidase, putative {ECO:0000313:EMBL: EED21226.1} ; EC=3.2.1.21{ECO:0000313: EMBL:EED21226.1} ; EC=3.2.1.. 21{ECO:0000313:EMBL:EED21226.1} ;".
Shiela E. Unkles et al., "The development of a homologous transformation system for Aspergillus oryzae based on the nitrate assimilation pathway: A convenient and general selection system for filamentous fungal transformation", Mol. Gen. Genet., vol. 218, pp. 99-104 (1989).
Office Action mailed Jan. 14, 2016 for U.S. Appl. No. 14/324,340.
Office Action mailed Jan. 14, 2016 for U.S. Appl. No. 14/324,300.

*Primary Examiner* — Maryam Monshipouri
(74) *Attorney, Agent, or Firm* — Carrier Blackman & Associates, P.C.; Joseph P. Carrier; Fulchand P. Shende

(57) ABSTRACT

The present invention relates to a polypeptide which has β-glucosidase activity, and which includes an amino acid sequence represented by SEQ ID NO: 1, a polypeptide including an amino acid sequence in which one or several amino acids are deleted, substituted, or added in the amino acid sequence represented by SEQ ID NO: 1, or a polypeptide including an amino acid sequence having 91% or greater sequence identity with the amino acid sequence represented by SEQ ID NO: 1. According to the present invention, a novel β-glucosidase enzyme derived from *Acremonium cellulolyticus*, a polynucleotide encoding the β-glucosidase, an expression vector for expressing the β-glucosidase, a transformant incorporated with that expression vector, and a method for producing a cellulose degradation product using the β-glucosidase can be provided.

7 Claims, 4 Drawing Sheets

β-GLUCOSIDASE

TECHNICAL FIELD

The present invention relates to a β-glucosidase enzyme derived from *Acremonium cellulolyticus*. More particularly, the present invention relates to a novel β-glucosidase, a polynucleotide that encodes the β-glucosidase, an expression vector for expressing the β-glucosidase, a transformant incorporated with the expression vector, and a method for producing a cellulose degradation product using the β-glucosidase.

The present application claims priority on the basis of Japanese Patent Application No. 2013-143259, filed on Jul. 9, 2013, the contents of which are incorporated herein by reference.

BACKGROUND ART

Recently, the development of alternative energy to oil is a very important issue, because of the concern related to transportation energy supply, such as large increases in oil prices and the petroleum depletion prediction in the near future (peak oil), as well as environmental problems such as global warming and aerial pollution. Plant biomass, or lignocellulose, is the most plentiful renewable energy source on earth, which is expected to serve as an alternative source to oil. The main components in the dry weight of biomass are polysaccharides such as celluloses and hemicelluloses, and lignin. For example, polysaccharides are used as a biofuel or a raw material of chemical products, after being hydrolyzed into monosaccharides such as glucose or xylose by glycoside hydrolases which are collectively referred to as cellulase enzymes.

Consequently, in the field of biorefining, it is important to develop a diverse range of highly active cellulase enzymes in order to efficiently carry out enzymatic hydrolysis treatment on cellulose-based biomass.

Lignocellulose is recalcitrant due to its highly complicated structures, and is hard to degrade with a single cellulolytic enzyme. Lignocellulose degradation to sugar requires at least three types of enzymes: endoglucanases (cellulase or endo-1,4-β-D-glucanase, EC 3.2.1.4) which randomly cut internal sites on cellulose chain, cellobiohydrolases (1,4-β-cellobiosidase or cellobiohydrolase, EC 3.2.1.91) which act as an exo-cellulase on the reducing or non-reducing ends of cellulose chain and release cellobiose as major products, and β-glucosidases (EC 3.2.1.21) which hydrolyze cellobiose to glucose. Besides, it is thought to be necessary to have an appropriate blending of a plurality of enzymes including xylanase (endo-1,4-β-xylanase, EC 3.2.1.8) which is a hemicellulase and other plant cell wall degrading enzymes.

On the other hand, *Acremonium cellulolyticus* is a filamentous fungus that produces a potent hydrolytic cellulase, and two types of cellobiohydrolase genes, 3 types of β-glucosidase genes and 7 types of endoglucanase genes have currently been isolated therefrom (see, for example, Patent Document 1). Endoglucanase is one of the glycoside hydrolases associated with the process of producing monosaccharides by randomly cleaving and degrading celluloses or lignocelluloses such as hemicellulose.

PRIOR ART DOCUMENTS

Patent Documents

[Patent Document 1] Japanese Unexamined Patent Application, First Publication No. 2010-148427

DISCLOSURE OF THE INVENTION

Problems to be Solved by the Invention

An object of the present invention is to provide a novel β-glucosidase derived from *Acremonium cellulolyticus*, a polynucleotide that encodes the β-glucosidase, an expression vector for expressing the β-glucosidase, a transformant incorporated with the expression vector, and a method for producing a cellulose degradation product using the β-glucosidase.

Means for Solving the Problems

As a result of conducting extensive studies to develop a novel cellulase enzyme having high activity, the inventors of the present invention isolated and identified a novel cellulase gene from *Acremonium cellulolyticus*, thereby leading to completion of the present invention.

[1] A first aspect of the present invention is:
a β-glucosidase having a β-glucosidase catalytic domain which includes: (A) a polypeptide including the amino acid sequence represented by SEQ ID NO. 1; (B) a polypeptide having β-glucosidase activity including an amino acid sequence obtained by deleting, substituting or adding one or a plurality of amino acids in the amino acid sequence represented by SEQ ID NO: 1; or (C) a polypeptide including an amino acid sequence having 91% or greater sequence identity with the amino acid sequence represented by SEQ ID NO: 1, and having β-glucosidase activity.

[2] The β-glucosidase of [1] above preferably has β-glucosidase activity at pH 3.0 to pH 5.5 and at a temperature of 30° C. to 75° C. that uses p-Nitrophenyl β-D-glucopyranoside as a substrate.

[3] A second aspect of the present invention is a polynucleotide including a region that encodes a β-glucosidase catalytic domain which includes: (a) a base sequence that encodes a polypeptide including the amino acid sequence represented by SEQ ID NO: 1; (b) a base sequence that encodes a polypeptide including an amino acid sequence in which one or several amino acids are deleted, substituted, or added in the amino acid sequence represented by SEQ ID NO: 1, and having β-glucosidase activity; (c) a base sequence that encodes a polypeptide including an amino acid sequence having 91% or greater sequence identity with the amino acid sequence represented by SEQ ID NO: 1, and having β-glucosidase activity; or (d) abase sequence of a polynucleotide which hybridizes with a polynucleotide comprising the base sequence represented by SEQ ID NO: 2 under a stringent condition, and being a base sequence that encodes a polypeptide having β-glucosidase activity.

[4] A third aspect of the present invention is an expression vector, which is incorporated with the polynucleotide described in [3] above, and which is able to express a polypeptide having β-glucosidase activity in a host cell.

[5] A fourth aspect of the present invention is a transformant, which is introduced with the expression vector described in [4] above.

[6] The transformant described in [5] above is preferably a eukaryotic microbe.

[7] The transformant described in [5] above is preferably a filamentous fungus.

[8] A fifth aspect of the present invention is a method for producing a β-glucosidase, including: generating a polypeptide having β-glucosidase activity in the transformant described in any one of [5] to [7] above.

[9] A sixth aspect of the present invention is a cellulase mixture, including: the β-glucosidase described in [1] or [2]

above or a β-glucosidase produced by the method for producing a β-glucosidase described in [8] above, and at least one type of other cellulases.

[10] A seventh aspect of the present invention is a method for producing a cellulose degradation product including generating a cellulose degradation product by contacting a cellulose-containing material with the β-glucosidase described in [1] or [2] above or a β-glucosidase produced by the method for producing a β-glucosidase described in [8] above.

[11] In the method for producing a cellulose degradation product described in [10] above, at least one type of other cellulases are preferably further contacted with the cellulose-containing material.

[12] In the method for producing a cellulose degradation product described in [10] above, a cellobiohydrolase including an amino acid sequence represented by SEQ ID NO: 11 and an endoglucanase including an amino acid sequence represented by SEQ ID NO: 12 are preferably further contacted with the cellulose-containing material.

[13] In the method for producing a cellulose degradation product described in [10] above, a cellobiohydrolase including an amino acid sequence represented by SEQ ID NO: 11, an endoglucanase comprising an amino acid sequence represented by SEQ ID NO: 12, and at least one type of hemicellulases are preferably further contacted with the cellulose-containing material.

Effects of the Invention

The β-glucosidase according to the present invention is a novel β-glucosidase enzyme derived from *Acremonium cellulolyticus*. Since this β-glucosidase has hydrolase activity on cellulose, it is particularly preferable for enzymatic hydrolysis treatment of cellulose-based biomass.

In addition, the polynucleotide, the expression vector incorporated with the polynucleotide, and the transformant introduced with the expression vector according to the present invention are preferably used in the production of the β-glucosidase according to the present invention.

BEST MODE FOR CARRYING OUT THE INVENTION

[β-Glucosidase]

Figure 1:
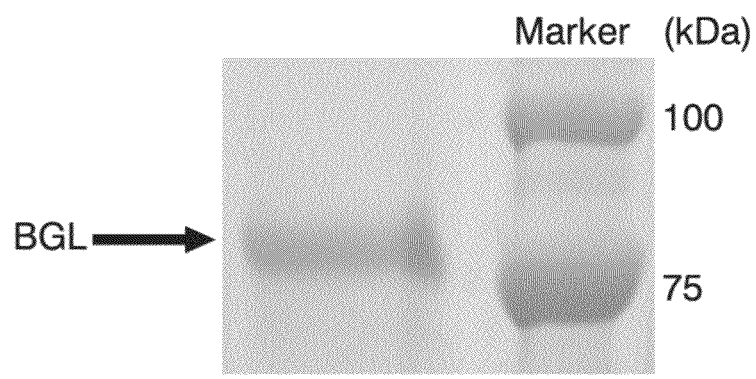
FIG. 1 shows the SDS-PAGE analysis result of the enzyme sample (BGL) in Example 1.

The inventors of the present invention isolated and identified a gene encoding a novel β-glucosidase from cDNA synthesized by a reverse transcription reaction using mRNA recovered from *Acremonium cellulolyticus* as template, designated that gene as BGL gene, and designated β-glucosidase encoded by that gene as BGL. The amino acid sequence of BGL is shown in SEQ ID NO: 1, and the base sequence encoding BGL (base sequence of the coding region of BGL gene) is shown in SEQ ID NO: 2.

In general, in a protein having some kind of bioactivity, one or two or more of amino acids can be deleted, substituted, or added without deteriorating the bioactivity. That is, in BGL, one or two or more of amino acids can also be deleted, substituted, or added without deteriorating the β-glucosidase activity.

That is, the β-glucosidase of a first aspect of the present invention is a β-glucosidase having a β-glucosidase catalytic domain which includes any one of (A) to (C) indicated below:

(A) a polypeptide including the amino acid sequence represented by SEQ ID NO. 1;

(B) a polypeptide including an amino acid sequence in which one or several amino acids are deleted, substituted, or added in the amino acid sequence represented by SEQ ID NO: 1, and having β-glucosidase activity; or (C) a polypeptide including an amino acid sequence having 91% or greater sequence identity with the amino acid sequence represented by SEQ ID NO: 1, and having β-glucosidase activity.

In the present invention and description of the present application, the deletion of an amino acid in a polypeptide refers to the deletion (or removal) of a portion of the amino acids that compose a polypeptide.

In the present invention and description of the present application, the substitution of an amino acid in a polypeptide refers to the substitution of an amino acid that composes a polypeptide with another amino acid.

In the present invention and description of the present application, the addition of an amino acid in a polypeptide refers to the insertion of a new amino acid in a polypeptide.

In the polypeptide of the aforementioned (B), the number of amino acids to be deleted, substituted, or added in the amino acid sequence represented by SEQ ID NO: 1 is preferably 1 to 20, more preferably 1 to 10 and even more preferably 1 to 5. The position(s) of the amino acid(s) to be deleted, substituted, or added in each amino acid sequence is (are) not specifically limited as long as the polypeptide including the amino acid sequence in which amino acids have been deleted, substituted, or added retains β-glucosidase activity.

In the polypeptide of the aforementioned (C), although there are no particular limitations on the sequence identity with the amino acid sequence represented by SEQ ID NO: 1 is not specifically limited as long as it is 91% or greater and less than 100%, although it is preferable to be 93% or greater and less than 100%, more preferably 95% or greater and less than 100%, and even more preferably 98% or greater and less than 100%.

Note that, the sequence identity (homology) between two amino acid sequences is obtained such that: the two amino acid sequences are juxtaposed while having gaps in some parts accounting for insertion and deletion so that the largest number of corresponding amino acids can be matched, and the sequence identity is deemed to be the proportion of the matched amino acids to the whole amino acid sequences excluding the gaps, in the resulting alignment. The sequence identity between amino acid sequences can be obtained by using a variety of homology search software commonly known in the art. The sequence identity value of amino acid sequences in the present invention is obtained by calculation on the basis of an alignment obtained from the maximum matching function of the publicly known homology search software, Genetyx Ver. 11.0.

The polypeptides of the aforementioned (B) and (C) may be artificially designed, or may also be homologues of BGL, or partial proteins thereof.

The polypeptides of the aforementioned (A) to (C) may be respectively synthesized in a chemical manner based on the amino acid sequence, or may also be produced by a protein expression system using the polynucleotide according to the second aspect of the present invention that will be described later. In addition, the polypeptides of the aforementioned (B) and (C) can also be respectively synthesized artificially based on a polypeptide including the amino acid sequence represented by SEQ ID NO: 1, by using a gene recombination technique to introduce amino acid mutation(s).

The β-glucosidase according to the present invention uses a glucan containing a β-glycoside bond as a substrate. Examples of substrates of the β-glucosidase according to the present invention include crystalline cellulose, carboxymethyl cellulose (CMC), glucans composed of β-1,4 bonds such as cellobiose, glucans composed of β-1,3 bonds and β-1,4 bonds, and glucans composed of β-1,6 bonds such as gentiobiose.

The β-glucosidase according to the present invention exhibits β-glucosidase activity within a temperature range of 20° C. to 60° C. The β-glucosidase according to the present invention exhibiting β-glucosidase activity within a temperature range of 20° C. to 75° C. is preferable, and within a temperature range of 20° C. to 80° C. is more preferable. Moreover, the β-glucosidase having an optimum temperature range of β-glucosidase activity according to the present invention within a temperature range of 30° C. to 75° C. is preferable, within a temperature range of 40° C. to 70° C. is more preferable, and within a temperature range of 40° C. to 65° C. is ever more preferable.

The β-glucosidase activity according to the present invention refers to activity that uses a glucan containing a β-glycoside bond as a substrate and forms a monosaccharide by hydrolyzing the aforementioned substrate.

Although varying depending on the reaction temperature, the optimum pH of the β-glucosidase according to the present invention is within the range of pH 2.0 to pH 6.0, preferably within the range of pH 2.5 to pH 5.5, and more preferably within the range of pH 2.5 to pH 4.0. The β-glucosidase according to the present invention preferably exhibits β-glucosidase activity at least within the range of pH 3.0 to pH 5.5, preferably within the range of pH 2.5 to pH 6.0, and more preferably within the range of pH 2.0 to pH 6.0.

The β-glucosidase according to the present invention exhibits high β-glucosidase activity even in an acidic environment. For example, in the case of using PNPG (p-Nitrophenyl 3-D-glucopyranoside) as a substrate, the β-glucosidase according to the present invention exhibits high β-glucosidase activity in an environment at pH 3.0 to pH 5.5. The β-glucosidase of the present invention preferably exhibits PNPG decomposition activity at pH 3.0 to pH 5.5 and a temperature of 30° C., more preferably at pH 3.0 to pH 5.5 and a temperature of 30° C. to 75° C., and even more preferably at pH 3.0 to pH 5.5 and a temperature of 25° C. to 80° C.

The β-glucosidase according to the present invention may also have cellulose hydrolysis activity other than β-glucosidase activity. Examples of other cellulose hydrolysis activity include cellobiohydrolase activity, endoglucanase activity and xylanase activity.

The β-glucosidase according to the present invention may be an enzyme consisting only of a β-glucosidase catalytic domain which includes any one of the polypeptides of the aforementioned (A) to (C), or may also include other regions. Examples of other regions include regions other than a β-glucosidase catalytic domain of a known β-glucosidase. For example, the β-glucosidase according to the present invention also includes an enzyme obtained by substituting a β-glucosidase catalytic domain in a known β-glucosidase with a polypeptide of the aforementioned (A) to (C).

The β-glucosidase according to the present invention may also have a signal peptide able to transport it to a specific region to effect localization within a cell, or a signal peptide to effect extracellular secretion, for example, at the N-terminal or C-terminal thereof. Examples of such signal peptides include endoplasmic reticulum signal peptide, a nuclear transport signal peptide and a secretory signal peptide. The addition of a signal peptide to the N-terminal or C-terminal of the aforementioned β-glucosidase allows β-glucosidase expressed in a transformant to be secreted outside a cell or localized in the endoplasmic reticulum or other locations in a cell.

The endoplasmic reticulum retention signal peptide is not particularly limited, as long as it is a peptide enabling to retain the polypeptide within the endoplasmic reticulum, and a publicly known endoplasmic reticulum retention signal peptide can be appropriately used. The endoplasmic reticulum retention signal peptide can be exemplified by, for example, a signal peptide including a HDEL amino acid sequence, or the like.

In addition, various types of tags may be added to, for example, the N-terminal or C-terminal of the β-glucosidase according to the present invention, so as to enable easy and convenient purification in the case of having produced the aforementioned β-glucosidase using an expression system. Examples of tags used include those commonly used in the expression or purification of recombinant protein, such as a His tag, a HA (hemagglutinin) tag, a Myc tag or a Flag tag.

Moreover, the β-glucosidase according to the present invention may also have other functional domains provided β-glucosidase activity derived from the polypeptides of the aforementioned (A) to (C) is not impaired. Examples of other functional domains include cellulose binding modules. Examples of the cellulose binding modules include cellulose binding modules retained by a known protein or those that have undergone suitable modification.

In the case the β-glucosidase according to the present invention has a functional domain other than a β-glucosidase catalytic domain, the other functional domain may be located upstream (N-terminal side) or downstream (C-terminal side) from the β-glucosidase catalytic domain. In addition, the other functional domain and the β-glucosidase catalytic domain may be directly linked, or linked via a linker sequence of an appropriate length.

[Polynucleotide that Encodes β-Glucosidase]

The polynucleotide of a second aspect of the present invention encodes the β-glucosidase of the first aspect of the present invention. This β-glucosidase can be produced by using an expression system of a host by introducing an expression vector incorporated with the polynucleotide into the host.

More specifically, the polynucleotide of the second aspect of the present invention is a polynucleotide having a region that encodes a β-glucosidase catalytic domain which includes any one of the following base sequences (a) to (d):

(a) a base sequence that encodes a polypeptide including the amino acid sequence represented by SEQ ID NO: 1;

(b) a base sequence that encodes a polypeptide including an amino acid sequence in which one or several amino acids are deleted, substituted, or added in the amino acid sequence represented by SEQ ID NO: 1, as well as having β-glucosidase activity;

(c) a base sequence that encodes a polypeptide including an amino acid sequence having 91% or greater sequence identity with the amino acid sequence represented by SEQ ID NO: 1, as well as having β-glucosidase activity; or (d) a base sequence of a polynucleotide that hybridizes under stringent conditions with a polynucleotide including the base sequence represented by SEQ ID NO: 2, as well as being a base sequence that encodes a polypeptide having β-glucosidase activity.

Note that, the sequence identity (homology) between two base sequences is obtained such that: the two base sequences are juxtaposed while having gaps in some parts accounting for insertion and deletion so that the largest number of corresponding bases can be matched, and the sequence identity is deemed to be the proportion of the matched bases to the whole base sequences excluding the gaps, in the resulting alignment. The sequence identity between base sequences can be obtained by using a variety of homology search software commonly known in the art. The sequence identity value between base sequences in the present invention is obtained by calculation on the basis of an alignment obtained from the maximum matching function of the publicly known homology search software, GenetyxVer. 11.0.

In addition, in the present invention and description of the present application, the term "stringent conditions" refers to, for example, the method described in NATURE PROTOCOL (VOL. 1, No, 2, p. 518 to 525) (Published online: 27 Jun. 2006, doi:10.1038/nprot.2006.73). An example thereof includes conditions under which hybridization is carried out by incubating for several hours to overnight at a temperature of 40° C. to 65° C. in a hybridization buffer composed of 6×SSC (composition of 20×SSC: 3 M sodium chloride, 0.3 M citric acid solution), 5×Denhardt's solution (composition of 100×Denhardt's solution: 2% by mass bovine serum albumin, 2% by mass ficoll, 2% by mass polyvinylpyrrolidone), 0.5% by mass SDS, and 0.1 mg/mL salmon sperm DNA.

Sequence identity of the base sequence of the aforementioned (d) with the base sequence represented by SEQ ID NO: 2 is, for example, 85% or greater and not greater than 100%, preferably 90% or greater and not greater than 100%, more preferably 93% or greater and not greater than 100%, and even more preferably 95% or greater and not greater than 100%.

In the base sequences of the aforementioned (a) to (d), a degenerate codon having a high frequency of usage in the host is preferably selected for the degenerate codon. For example, the base sequence of the aforementioned (a) may be a base sequence represented by SEQ ID NO: 2 or a base sequence that has been modified to a codon having a high frequency of usage in the host without altering the encoded amino acid sequence (SEQ ID NO: 1). Note that, these codons can be altered by a publicly known gene recombination technique.

The polynucleotide including the base sequence represented by SEQ ID NO: 2 may be chemically synthesized based on base sequence information, or may be obtained a region including a β-glucosidase catalytic domain in the BGL gene of *Acremonium cellulolyticus* from nature by using a gene recombination technique. The full length of the BGL gene or the partial region thereof can be obtained by, for example, collecting a sample containing *Acremonium cellulolyticus* from nature, using as template cDNA synthesized by a reverse transcription reaction by using mRNA recovered from the sample as a template, and carrying out PCR using a forward primer and reverse primer designed in accordance with ordinary methods based on the base sequence represented by SEQ ID NO: 2.

For example, the polynucleotides including the base sequence of the aforementioned (b), (c) or (d) can each be artificially synthesized by deleting, substituting or adding one or two or more of bases to a polynucleotide including the base sequence represented by SEQ ID NO: 2.

In the present invention and description of the present application, the deletion of a base in a polynucleotide refers to the deletion (or removal) of a portion of the nucleotides that compose a polypeptide.

In the present invention and description of the present application, the substitution of a base in a polynucleotide refers to the substitution of a base that composes a polynucleotide with another base.

In the present invention and description of the present application, the addition of a base in a polynucleotide refers to the insertion of a new base in a polynucleotide.

The polynucleotide of the second aspect of the present invention may only have a region that encodes a β-glucosidase catalytic domain, or may also have a region that encodes another functional domain such as a cellulose binding module, a linker sequence, various types of signal peptides, or various types of tags in addition to that region.

[Expression Vector]

The expression vector of the third aspect of the present invention is incorporated with the aforementioned polynucleotide of the second aspect of the present invention, and is capable of expressing a polypeptide having β-glucosidase activity in host cells. That is, the expression vector is an expression vector in which the aforementioned polynucleotide of the second aspect of the present invention is incorporated in a state that enables expression of the aforementioned β-glucosidase of the first aspect of the present invention.

In the present invention and description of the present application, an expression vector refers to a vector that contains DNA having a promoter sequence, DNA having a sequence for incorporating foreign DNA and DNA having a terminator sequence starting from the upstream side.

More specifically, an expression cassette including DNA having a promoter sequence, the aforementioned polynucleotide of the second aspect of the present invention, and DNA having a terminator sequence is required to be incorporated in the expression vector starting from the upstream side. Note that, the polynucleotide can be incorporated in the expression vector using well-known gene recombination technique. A commercially available expression vector preparation kit may also be used to incorporate the polynucleotide into the expression vector.

The expression vector may be that which is introduced into prokaryotic cells such as *Escherichia coli* or may be that which is introduced into eukaryotic cells such as yeast, filamentous fungi, cultured insect cells, cultured mammalian cells or plant cells. Arbitrary expression vectors normally used corresponding to each host can be used for these expression vectors.

An expression vector introduced into prokaryotic cells or an expression vector introduced into eukaryotic microbes such as yeast or filamentous fungi is preferable for the expression vector according to the present invention, an expression vector introduced into eukaryotic microbes is more preferable, an expression vector introduced into a filamentous fungus is even more preferable, and an expression vector introduced into *aspergillus* is even much more preferable. The use of an expression system in prokaryotic cells or eukaryotic microbes makes it possible to produce the β-glucosidase according to the present invention more easily and conveniently with high yield. In addition, since the β-glucosidase enzyme including the amino acid sequence represented by SEQ ID NO: 1 is an enzyme that is inherently possessed by the filamentous fungus *Acremonium cellulolyticus*, β-glucosidase can be synthesized that more closely approximates natural β-glucosidase by expressing the β-glucosidase using an expression system of a eukaryotic microbes such as filamentous fungus.

The expression vector according to the present invention is preferably an expression vector that is also incorporated with a drug resistance gene in addition to the aforementioned polynucleotide of the second aspect of the present invention. This is because it makes it easy to screen between host organisms that have been transformed by the expression vector and host organisms that have not been transformed. Examples of drug resistance genes include ampicillin resistance gene, kanamycin resistance gene, hygromycin resistance gene, or the like.

[Transformant]

The transformant of a fourth aspect of the present invention is introduced with the aforementioned expression vector of the third aspect of the present invention. The aforementioned β-glucosidase of the first aspect of the present invention can be expressed in this transformant. The β-glucosidase according to the present invention can be expressed in a wide range of expression hosts such as *Escherichia coli*, yeast, filamentous fungus or the chloroplasts of higher plants.

There are no particular limitations on the method used to prepare a transformant using an expression vector, and preparation can be carried out according to a method normally used in the case of preparing transformants. Examples of these methods include the PEG (polyethylene glycol)-calcium method, *Agrobacterium* method, particle gun method and electroporation, and the like. Among these, the PEG-calcium method or *Agrobacterium* method is preferable in the case the host is a filamentous fungus.

In the case of using prokaryotic cells, yeast, filamentous fungi, cultured insect cells or cultured mammalian cells and the like for the host, the resulting transformant can typically be cultured in accordance with ordinary methods in the same manner as the host prior to transformation.

Eukaryotic cells such as yeast, filamentous fungi, cultured insect cells or cultured mammalian cells and the like are preferable as hosts introduced with the expression vector. Since glycosylation modification is carried out on proteins in eukaryotic cells, the use of a transformant of eukaryotic cells enables the production of β-glucosidase having superior thermostable in comparison with the case of using a transformant of prokaryotic cells. In particular, in the case the transformant is a filamentous fungus such as an *aspergillus* and a eukaryotic microbe such as a filamentous fungus or yeast, β-glucosidase having superior thermostable can be produced comparatively easily and conveniently with high yield.

In the transformant according to the present invention, the expression cassette for expressing the β-glucosidase according to the present invention derived from the aforementioned expression vector of the third aspect of the present invention may be incorporated in a genome or may be present independently outside the genome.

[Method for Producing β-Glucosidase]

The method for producing β-glucosidase of a fifth aspect of the present invention is a method for producing β-glucosidase in the aforementioned transformant of the fourth aspect of the present invention. The β-glucosidase according to the present invention is constantly expressed in a transformant produced using an expression vector in which the aforementioned polynucleotide of the second aspect of the present invention is incorporated downstream from a promoter not having the ability to control the timing of expression and the like. On the other hand, by carrying out suitable induction treatment on a transformant producing a so-called expression inducible promoter, which induces expression according to a specific compound or temperature conditions and the like, under those respective conditions for inducing expression, β-glucosidase can be expressed in the concerned transformant.

There are no particular limitations on the method used to extract or purify β-glucosidase from the transformant provided it is a method that does not impair the activity of the β-glucosidase, and extraction can be carried out by a method normally used in the case of extracting polypeptides from cells or biological tissue. An example of such a method includes consists of immersing the transformant in a suitable extraction buffer to extract β-glucosidase followed by separating the extract and the solid residue. The extraction buffer preferably contains a solubilizing agent such as a surfactant. In the case the transformant is a plant, the transformant may be preliminarily shredded or crushed prior to immersing in extraction buffer. In addition, a known solid-liquid separation treatment can be used to separate the extract and solid residue, such as filtration, compression filtration or centrifugal separation, and the transformant may be pressed while still immersed in the extraction buffer. The β-glucosidase in the extract can be purified using a commonly known purification method such as salting-out, ultrafiltration or chromatography.

In the case the β-glucosidase according to the present invention has been expressed in a state of having a secretory signal peptide in the transformant, after having cultured the transformant, a solution can be easily and conveniently obtained that contains β-glucosidase by recovering culture supernatant from the resulting culture while excluding the transformant. In addition, in the case the β-glucosidase according to the present invention has a tag such as a His tag, β-glucosidase present in an extract or culture supernatant can be easily and conveniently purified by affinity chromatography utilizing that tag.

Namely, the method for producing β-glucosidase of the present invention includes the production of β-glucosidase in a transformant of the aforementioned fourth aspect of the present invention, and extraction and purification of the aforementioned β-glucosidase from the aforementioned transformant as desired.

[Cellulase Mixture]

The cellulase mixture of the sixth aspect of the present invention includes the aforementioned β-glucosidase of the first aspect of the present invention or β-glucosidase produced according to the aforementioned method for producing β-glucosidase of the fifth aspect of the present invention, and at least one type of other cellulases. The β-glucosidase produced according to the aforementioned method for producing β-glucosidase of the fifth aspect of the present invention may be in a state of being included in a transformant or may have been extracted or purified from a transformant. Glucans containing β-1,4 bonds such as cellulose can be degraded more efficiently by using the β-glucosidase according to the present invention in a cellulose degradation reaction in the form of a mixture with other cellulase.

There are no particular limitations on the cellulase other than the aforementioned β-glucosidase contained in the cellulase mixture provided it has cellulose hydrolysis activity.

Examples of cellulases other than the aforementioned β-glucosidase contained in the cellulase mixture include hemicellulases such as xylanase or β-xylosidase, endoglucanases, cellobiohydrolases, or the like. The cellulase mixture according to the present invention preferably contains at least one of hemicellulase and cellobiohydrolase, and more preferably contains both hemicellulase and cellobiohydrolase. In particular, the cellulase mixture preferably contains at least one or more types of cellulases selected from the group consisting of xylanase, β-xylosidase, endoglucanase and cellobiohydrolase, and more preferably contains all of xylanase, β-xylosidase, endoglucanase and cellobiohydrolase collectively.

[Method for Producing Cellulose Degradation Product]

The method for producing a cellulose degradation product of a seventh aspect of the present invention is a method for obtaining a degradation product by degrading cellulose with the β-glucosidase according to the present invention. More specifically, a cellulose degradation product is produced by contacting a material containing cellulose with the aforementioned β-glucosidase of the first aspect of the present invention, the aforementioned transformant of the fourth aspect of the present invention or β-glucosidase produced according to the aforementioned method for producing β-glucosidase of the fifth embodiment of the present invention.

There are no particular limitations on the material containing cellulose provided it contains cellulose. Examples of this material include cellulose biomass such as weeds or agricultural waste and used paper. The material containing cellulose is preferably subjected to physical treatment such as crushing or shredding, chemical treatment such as treatment with acid or alkali, or treatment by immersing or dissolving in a suitable buffer prior to contacting with the β-glucosidase according to the present invention.

The reaction conditions of the cellulose hydrolysis reaction carried out by the β-glucosidase according to the present invention are conditions that allow the β-glucosidase to exhibit β-glucosidase activity. For example, the reaction is preferably carried out at a temperature of 20° C. to 60° C. and a pH of 4 to 6 and more preferably carried out at a temperature of 25° C. to 55° C. at a pH of 4 to 6. The reaction time of the aforementioned hydrolysis reaction is suitably adjusted in consideration of such factors as the type of cellulose-containing material subjected to hydrolysis, the pretreatment method or the amount used. For example, the aforementioned hydrolysis reaction can be carried out over a reaction time of 10 minutes to 12 hours.

In addition to the β-glucosidase according to the present invention, at least one type of other cellulases are preferably used in the cellulose hydrolysis reaction. The same cellulases as those contained in the aforementioned cellulase mixture can be used for the other cellulases, and thermostable cellulase having cellulase activity at a temperature of 20° C. to 60° C. and a pH of 4 to 6 is preferable. In addition, the aforementioned cellulase mixture of the sixth aspect of the present invention may be used in the method for producing a cellulose degradation product instead of the aforementioned β-glucosidase of the first aspect of the present invention, the aforementioned transformant of the fourth aspect of the present invention, or β-glucosidase produced according to the aforementioned method for producing β-glucosidase of the fifth aspect of the present invention.

EXAMPLES

Although the following provides a more detailed explanation of the present invention by indicating examples thereof, the present invention is not limited to the following examples.

Example 1

(1) Construction of BGL *Aspergillus* Expression Vector
<Extraction of cDNA of *Acremonium cellulolyticus*>
*Acremonium cellulolyticus* strain H1 (acquired from the International Patent Organism Depository of the National Institute of Technology and Evaluation, accession number: FERM BP-11508, to be referred to as "strain H1") was inoculated onto PDB agar medium (plate medium obtained by adding 1.5% (w/v) of agarose to PDA medium (using Difco PDA broth)) followed by culturing for 1 week at a temperature of 30° C. The resulting bacterial cells were inoculated into PDA medium after cutting out the agar on which the cells were present to a diameter of 5 mm followed by shake-culturing at a temperature of 30° C. and 130 rpm. Bacterial cells recovered by centrifuging the culture for 10 minutes at 15000 rpm were washed twice with PDA medium to acquire a bacterial cell sample.

Next, beads were placed in a 2 mL volume plastic tube, crushing treatment for 90 seconds was carried out three times using a desktop bead-type crushing device (device name: Shake Master, Bio-Medical Science Co., Ltd.) to crush the cell sample, followed by extracting DNA using Isogen II (Nippon Gene Co., Ltd.). cDNA was synthesized from the extracted RNA using a cDNA synthesis kit (trade name: SMARTer™ RACE cDNA Amplification Kit, Clontech Laboratories, Inc.).

<cDNA of *Acremonium cellulolyticus* BGL>

A sequence encoding BGL (SEQ ID NO: 2) was amplified by PCR using the resulting cDNA as template and using a primer including the base sequence represented by SEQ ID NO: 3 shown in Table 1, a primer including the base sequence represented by SEQ ID NO: 4, and DNA polymerase (trade name: KOD-Plus, Toyobo Co., Ltd.). PCR consisted of carrying out one cycle consisting of 2 minutes at a temperature of 94° C. followed by carrying out 30 cycles consisting of 20 seconds at a temperature of 96° C., 30 seconds at a temperature of 60° C. and 5 minutes at a temperature of 72° C. The resulting PCR product was purified using the QIAquick PXR Purification Kit (Qiagen Inc.).

<Preparation of *E. coli* Vector pBR-niaD Containing niaD Gene>

PCR was carried out in the same manner as amplification of BGL cDNA with the exception of using genomic cDNA of *Aspergillus oryzae* strain RIB40 (acquired from the National Institute of Technology and Evaluation, NBRC number: 100959, to be referred to as "strain RIB40") as template, and using a primer including the base sequence represented by SEQ ID NO: 5 shown in Table 1 and a primer including the base sequence represented by SEQ ID NO: 6 to amplify cDNA of nitrate reductase gene niaD derived from *Aspergillus oryzae*.

After digesting the resulting PCR amplification product and *E. coli* plasmid pBR322 (Takara Bio Inc.) using restriction enzymes AvaI and NdeI at a temperature of 37° C., the digestion products were separated by agarose gel electrophoresis, and the target band was cut out followed by extracting and purifying from that piece of gel using the QIAquick Gel Extraction Kit (Qiagen Inc.) to obtain cDNA restriction enzyme-treated fragments of pBR322 and niaD. These DNA fragments were then linked using a DNA Ligation Kit (Takara Bio Inc.) and an *E. coli* strain JM109 (to be referred to as "strain JM109") was transformed by these DNA fragments. As a result, a transformant was obtained that was introduced with plasmid pBR-niaD (plasmid having the cDNA fragment of niaD inserted between restriction enzymes AvaI and NdeI of pBR322).

<Incorporation of agdA Terminator in pBR-niaD>

PCR was carried out in the same manner as amplification of BGL cDNA with the exception of using genomic DNA of RIB40 as template, and using a primer including the base sequence represented by SEQ ID NO: 7 shown in Table 1 and a primer including the base sequence represented by SEQ ID NO: 8 to amplify cDNA of the terminator region of agdA gene derived from an *aspergillus* (to also be referred to as "agdA terminator").

After digesting the resulting PCR amplification product and pBR-niaD using restriction enzymes SalI and AvaI at a temperature of 37° C., cDNA restriction enzyme-treated fragments of pBR-niaD and agdA terminator were obtained from the resulting digestion product in the same manner as the aforementioned preparation of pBR-niaD, and these DNA fragments were linked and a strain JM109 was transformed by these DNA fragments. As a result, a transformant was obtained that was introduced with plasmid pBR-agdAT-niaD (plasmid having the cDNA fragment of the agdA terminator inserted between restriction enzyme SalI and AvaI of pBR322-niaD).

<Incorporation of enoA Promoter in pBR-agdAT-niaD>

PCR was carried out in the same manner as amplification of BGL cDNA with the exception of using genomic DNA of RIB40 as template, and using a primer including the base sequence represented by SEQ ID NO: 9 shown in Table 1 and a primer including the base sequence represented by SEQ ID NO: 10 to amplify cDNA of the promoter region of enoA gene derived from an *aspergillus* (to also be referred to as "enoA promoter").

After digesting the resulting PCR amplification product and pBR-agdAT-niaD using restriction enzymes NheI and SalI at a temperature of 37° C., cDNA restriction enzyme-treated fragments of pBR-agdAT-niaD and enoA promoter were obtained from the resulting digestion product in the same manner as the aforementioned preparation of pBR-niaD, and these DNA fragments were linked and a strain JM109 was transformed by these DNA fragments. As a result, a transformant was obtained that was introduced with plasmid pBR-enoAP-agdAT-niaD (plasmid having the cDNA fragment of the enoA promoter inserted between restriction enzymes NheI and SalI of pBR322-agdAT-niaD).

TABLE 1

| SEQ ID No. | Base Sequence |
|---|---|
| 3 | TCCTCCAAGTTACCCATGAAGTCCCTCTCT |
| 4 | CGCTTCGTCGACCCCTCAATAACCCAACCC |
| 5 | ATGCTCGGGAGCTTTGGATTTCCTACGTCTTC |
| 6 | ATGCATATGTCGAGAGTGTTGTGTGGGTCAACG |
| 7 | ATGGTCGACGAAGCGTAACAGGATAGCCTAGAC |
| 8 | ATGCCCGAGAGTAACCCATTCCCGGTTCTCTAG |
| 9 | ATGGCTAGCAGATCTCGCGGCAGGGTTGAC |
| 10 | ATGGTCGACCCCGGGTAACTTGGAGGACGGAAGAAAAGAG |

<Incorporation of BGL Genomic DNA in pBR-enoAP-agdAT-niaD>

First, after digesting pBR-enoAP-agdAT-niaD using restriction enzyme SalI at a temperature of 30° C., an SmaI-treated fragment of pBR-enoAP-agdAT-niaD was obtained from the resulting digestion product in the same manner as the aforementioned preparation of pBR-niaD.

The SmaI-treated fragment and a sequence encoding BGL purified in the manner previously described were linked using the In-Fusion™ HD Cloning Kit (Clontech Laboratories, Inc.) to obtain plasmid pBR-enoAP-BGL-adgAT-niaD (BGL *Aspergillus oryzae* expression vector), and Stellar Competent Cells (Clontech Laboratories, Inc.) were transformed by this plasmid and a BGL *E. coli* transformant was obtained. The resulting transformant was cultured overnight at a temperature of 37° C. and 180 rpm in LB medium containing 100 μg/mL of ampicillin, and a large amount of pBR-enoAP-BGL-agdAT-niaD was prepared from the culture using the QIAquick Miniprep Kit (Qiagen Inc.).

(2) Production of *Aspergillus* Transformant Introduced with BGL *Aspergillus* Expression Vector

*Aspergillus oryzae* strain D300 (acquired from the National Institute of Technology and Evaluation) was transformed using the aforementioned plasmid pBR-enoAP-BGL-agdAT-niaD in accordance with the established PEG-calcium method (Mol. Gen. Genet., Vol. 218, pp. 99-104 (1989)). A transformant (BGL *aspergillus* transformed strain) was obtained by selecting the strain that was able to grow in Czapek-Dox medium (3% (w/v) dextrin, 0.1% (w/v) potassium dihydrogen phosphate, 0.2% (w/v) potassium chloride, 0.05% (w/v) magnesium sulfate, 0.001% (w/v) iron sulfate and 0.3% (w/v) sodium nitrate).

(3) Preparation of BGL from BGL *Aspergillus* Transformed Strain

The resulting BGL *aspergillus* transformed strain was allowed to form spores in Czapek-Dox medium followed by recovery of the spores in sterile water. The spores were inoculated into 100 mL of PD liquid medium contained in a 500 mL volume Erlenmeyer flask (2% (w/v) dextrin, 1% (w/v) polypeptone, 0.1% (w/v) casamino acids, 0.5% (w/v) potassium dihydrogen phosphate, 0.05% (w/v) magnesium sulfate and 0.1% (w/v) sodium nitrate) to a final spore concentration of $1 \times 10^4$/mL. After culturing the liquid for 3 days at a temperature of 30° C., the target gene product (BGL) was secreted and expressed in the medium. The culture liquid obtained after culturing was used as an enzyme sample.

BGL in the enzyme sample was confirmed by analysis by SDS-PAGE. SDS electrophoresis of the enzyme sample was carried out using 10% to 20% of Mini-Gradient gel (Atto Corp.). The enzyme sample and Tris-SDS β-ME sample treatment liquid (Atto Corp.) were mixed at a 1:1 ratio followed by treating for 5 minutes at a temperature of 100° C. and electrophoresing 20 μL of the mixture. Following completion of electrophoresis, the immobilized gel was stained with EzStain Aqua (Atto Corp.) to visualize the protein bands. Subsequently, an image of the gel was acquired using the ChemiDoc XRS Plus System (Bio-Rad Inc.). The acquired image was analyzed with Image Lab 2.0 software followed by quantification of the protein.

FIG. 1 shows the results of analyzing the enzyme sample (BGL) by SDS-PAGE. The right lane is the protein molecular weight marker, while the left lane is the enzyme sample. As a result, the enzyme sample was able to be confirmed to contain BGL having a molecular weight of approximately 80 kDa.

(4) Measurement of Enzyme Activity

Enzyme activity is indicated in units (U). 1 U is defined using the equation below as the amount of enzyme that produces 1 μmol of product from the substrate in 1 minute.

$$1\ U(\mu mol/min) = [sugar\ formed(\mu mol/L)] \times [reaction\ liquid\ volume(L)]/[reaction\ time(min)]$$

In addition, specific activity per 1 mg of protein is calculated using the following equation.

$$Specific\ activity(U/mg) = [Units(U)]/[amount\ of\ protein(mg)]$$

<Measurement of PNPG Degradation Activity>

PNPG (p-Nitrophenyl β-D-glucopyranoside) (Sigma-Aldrich Corp.) was used for the standard substrate. PNPG degradation activity is mainly used as an indicator β-glucosidase activity. In addition, a calibration curve was prepared from measured values of five dilution series (0 μM to 200 μM) prepared by suitably diluting a 1000 μmol/L PNP (p-nitrophenol) solution with 200 mM acetic acid buffer (pH 5.5).

More specifically, a number of 1.5 mL volume plastic tubes were first prepared equal to the number of samples measured, and liquids obtained by adding 615 μL of 200 mM acetic acid buffer (pH 5.5) and 50 μL of PNPG solution (3.4 mM, solvent: ultrapure water) to each tube followed by mixing well were adjusted to a temperature of 30° C. Next, 10 μL of enzyme sample were added to each tube to initiate the enzyme reaction, and after 15 minutes had elapsed since the start of the reaction, 625 μL of 0.2 M aqueous sodium carbonate solution were added and mixed to stop the reaction. Subsequently, 200 μl aliquots of the reaction solution were sampled from each tube followed by measuring the absorbance at 420 nm (A420). A sample treated in the same manner with the exception of adding 20 mM acetic acid buffer (pH 5.5) instead of enzyme sample was used as a blank during measurement of absorbance. PNP concentration was calculated from the A420 measured values and calibration curve, and specific activity was determined according to the equation below.

Specific activity(U/mg)=([PNP concentration(μmol/L)]×0.001×0.675/0.01)/(15×[amount of protein (mg)])

As a result, PNPG degradation activity (specific activity) of BGL produced in the BGL *aspergillus* transformed strain was 15.9 U/mg. That is, BGL produced in the BGL *aspergillus* transformed strain was confirmed to have PNPG degradation activity.

(5) Measurement of Hydrolysis Activity

The enzyme preparation used for measurement was prepared by containing the enzyme sample (BGL) prepared in the aforementioned section (3), cellobiohydrolase including the amino acid sequence represented by SEQ ID NO: 11, endoglucanase including the amino acid sequence represented by SEQ ID NO: 12, xylanase (Thermoascus aurantiacus-derived endo-1,4-beta-xylanase A, GenBank accession number: AAF24127) and β-xylosidase (*Thermotoga maritima*-derived β-xylosidase, Thermostable Enzyme Laboratory Co., Ltd.).

First, 25% (w/v) aqueous ammonia was mixed with finely crushed lignocellulose-based biomass in the form of corn stover to a weight ratio of 1:2.5 to obtain a substrate mixture containing corn stover and aqueous ammonia. Next, the aforementioned substrate mixture was held for 8 hours at a temperature of 80° C. to carry out hydrolysis pretreatment followed by separating the ammonia and adjusting to a pH of 4.5. Next, the corn stover content was adjusted to 20% by volume to obtain a hydrolysis pretreatment product used in the present example. The enzyme preparation containing BGL was added to this hydrolysis pretreatment product so that the final enzyme concentration per g of corn stover was 4.5 mg/g (corn stover) and allowed to react for 3 days at a temperature of 50° C. During the reaction, the reaction mixture was agitated by shaking at 160 rpm. In addition, a commercially available *Acremonium* species-derived hydrolysis enzyme mixture (trade name: *Acremonium* Cellulase, Meiji Seika Pharma Co., Ltd.) was used as a comparative control and allowed to react in the same manner.

Following completion of the reaction, the resulting hydrolysate was dispensed into a sampling tube and subjected to centrifugation treatment for 10 minutes at a temperature of 4° C. and 15,760×g. The resulting supernatant was transferred to a fresh 1.5 mL volume plastic tube, and after heat-treating for 5 minutes at a temperature of 95° C., was subjected to centrifugation treatment for 5 minutes at a temperature of 4° C. and 15,760×g. After again transferring the resulting supernatant to a fresh 1.5 mL volume plastic tube, the supernatant was filtered with a 0.2 μm (13 mm disk) filter. 0.2 mL of the filtrate were transferred to a vial, and sugar was detected by carrying out HPLC measurement under the conditions indicated below followed by evaluating sugar concentration. Glucose and xylose (Wako Pure Chemical Industries, Ltd., respectively) were used as sugar standards for HPLC.

Sugar concentration measurement device; Separator: Waters 2695 (Waters Corp.)
RI detector: Waters 2414 (Waters Corp.)
Column: Bio-Rad HPX-87P (Bio-Rad Inc.)
Sugar concentration measurement conditions:
Eluent: Ultrapure water
Flow rate: 0.6 mL/min
Column temperature: 85° C.
Detector temperature: 40° C.

Figure 2:
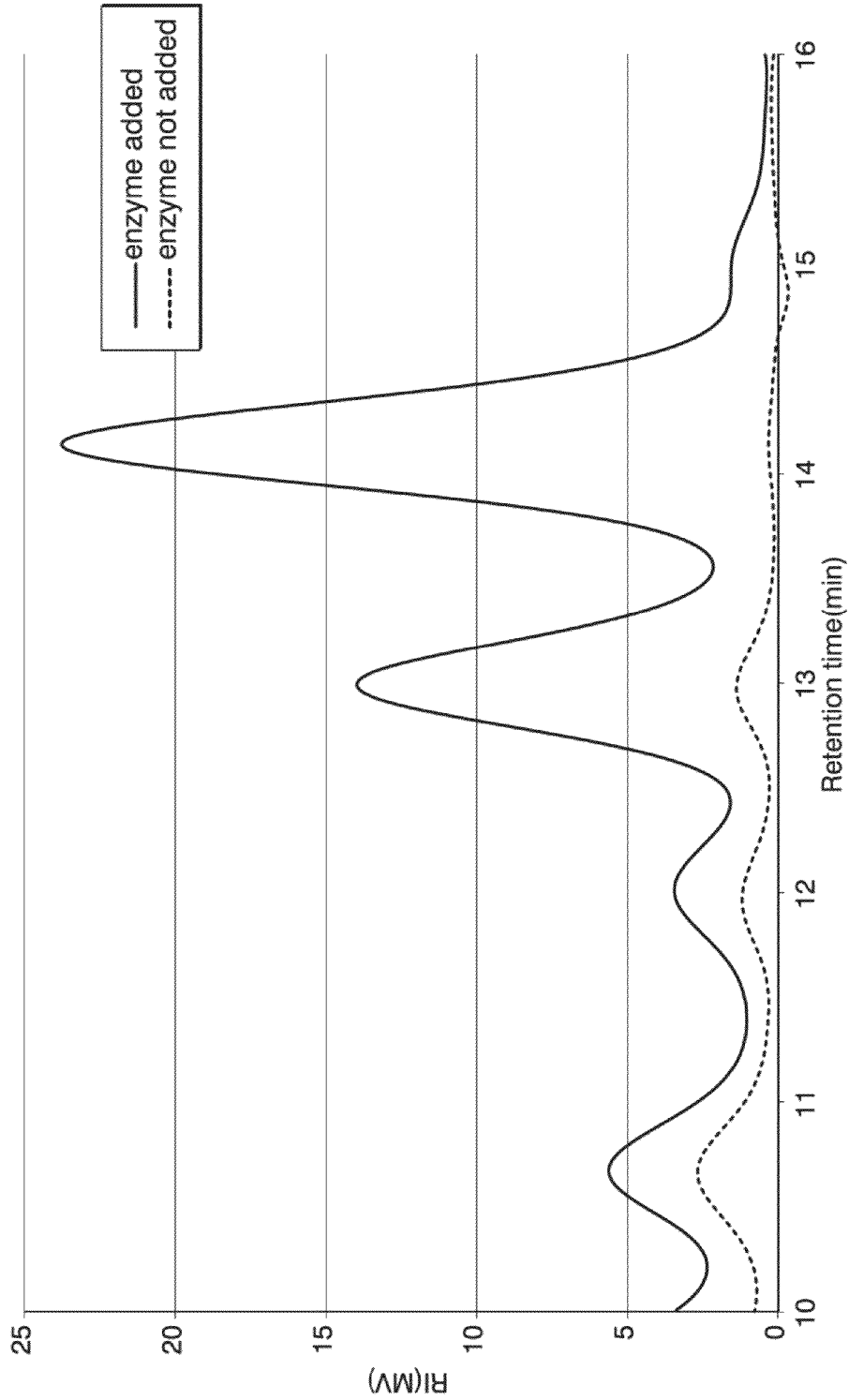
FIG. 2 is a chart indicating fractions obtained at retention times of 10 minutes to 16 minutes on an HPLC chromatogram of hydrolysates obtained by hydrolysis treatment of corn stover with an enzyme preparation in Example 1.

FIG. 2 indicates fractions obtained at retention times of 10 minutes to 16 minutes, at which disaccharides and monosaccharides are thought to elute, on an HPLC chromatogram of hydrolysates obtained from each reaction as detected with an RI detector by HPLC. In the chart, "enzyme added" indicates the results of a hydrolysate obtained following addition of the aforementioned enzyme preparation, while "enzyme not added" indicates the results of a hydrolysate treated in the same manner without adding the aforementioned enzyme preparation.

As a result, in contrast to the sugar concentration of hydrolysate (total concentration of glucose and xylose) in the case of using the commercially available hydrolysis enzyme mixture being 1.82% by mass, the value in the case of using the enzyme preparation containing BGL was 2.74% by mass, demonstrating that greater than approximately 1.5 times sugar was produced. On the basis of these results, the combined use of BGL of the present invention and other hydrolysis enzymes clearly allowed the obtaining of an enzyme mixture having a higher level of hydrolysis activity than conventional *Acremonium*-derived hydrolysis enzyme mixtures.

(6) Measurement of Enzyme Activity

<Measurement of Cellobiose Decomposition Activity>

Cellobiose decomposition activity and xylobiose activity were investigated using the enzyme sample prepared in the aforementioned section (3).

More specifically, 200 μL of a 0.03 M aqueous cellobiose solution and 190 μL of 200 mM acetic acid buffer (pH 5.5) were respectively added to two 1.5 mL volume plastic tubes and mixed well followed by pre-incubating for 5 minutes at a temperature of 30° C. Following pre-incubation, 10 μL of enzyme sample were added to one of the two tubes to initiate the enzyme reaction. After 90 minutes had elapsed since the start of the reaction, the solution in the tube was heat-treated for 5 minutes at a temperature of 95° C. to stop the enzyme reaction (duration of enzyme reaction: 90 minutes). 10 μL of enzyme sample were added to the remaining tube followed immediately by heat-treating the solution in the tube for 5 minutes at a temperature of 95° C. to stop the enzyme reaction (duration of enzyme reaction: 0 minutes).

In addition, 200 μL of a 0.014 M aqueous xylobiose solution and 190 μL of 200 mM acetic acid buffer (pH 5.5) were added to two 1.5 mL volume plastic tubes and mixed well followed by pre-incubating for 5 minutes at a temperature of 30° C., and then 100 μL of enzyme sample were added to the tube to initiate the enzyme reaction. 10 μl of enzyme sample were added to one of two tubes following pre-incubation to initiate an enzyme reaction. After 90 minutes had elapsed since the start of the reaction, the solution in the tube was heat-treated for 5 minutes at a temperature of 95° C. to stop the reaction (duration of enzyme reaction: 90 minutes). 10 µL of enzyme sample were added to the remaining tube followed immediately by heat-treating the solution in the tube for 5 minutes at a temperature of 95° C. to stop the enzyme reaction (duration of enzyme reaction: 0 minutes).

Following completion of the reactions, the four tubes were subjected to centrifugal separation treatment for 5 minutes at 15,760×g. After transferring the resulting supernatant to a fresh 1.5 mL volume plastic tube, the supernatant was filtered with a 0.2 µm (13 mm disk) filter. 0.2 mL of the filtrate were transferred to a vial, sugar was detected by carrying out HPLC measurement under the same conditions as in the aforementioned section (5), and specific activity per unit weight (U/mg) was calculated according to the equation below. Glucose and xylose (Wako Pure Chemical Industries, Ltd., respectively) were used as sugar standards for HPLC.

[Specific activity(U/mg)]=([glucose concentration (µmol/L)]×0.4/0.01)/(90×[amount of protein (mg)])

Figure 3:
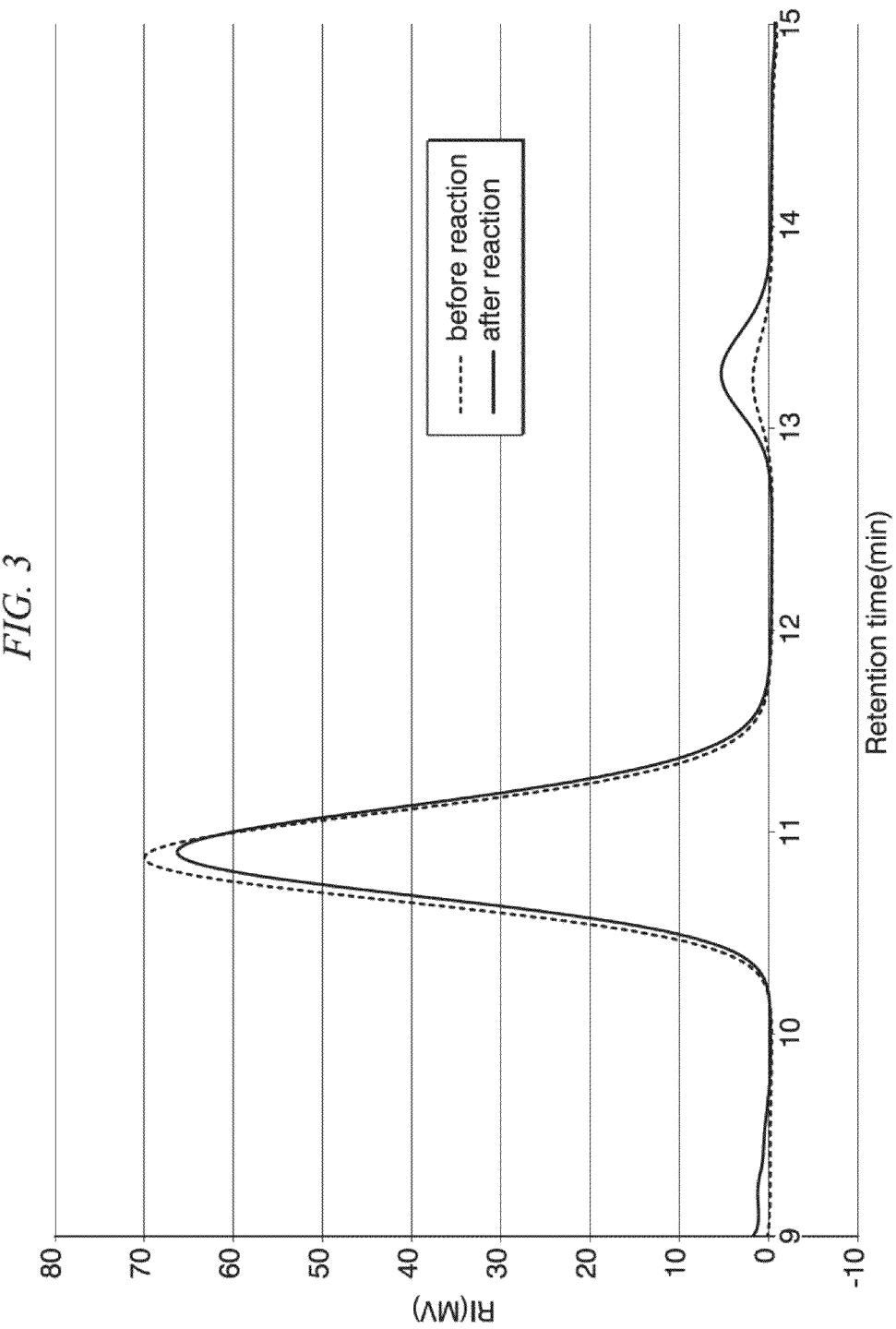
FIG. 3 is a chart indicating fractions obtained at retention times of 9 minutes to 15 minutes on an HPLC chromatogram of enzyme reaction liquids before and after an enzyme reaction of BGL using cellobiose as a substrate in Example 1.
Figure 4:
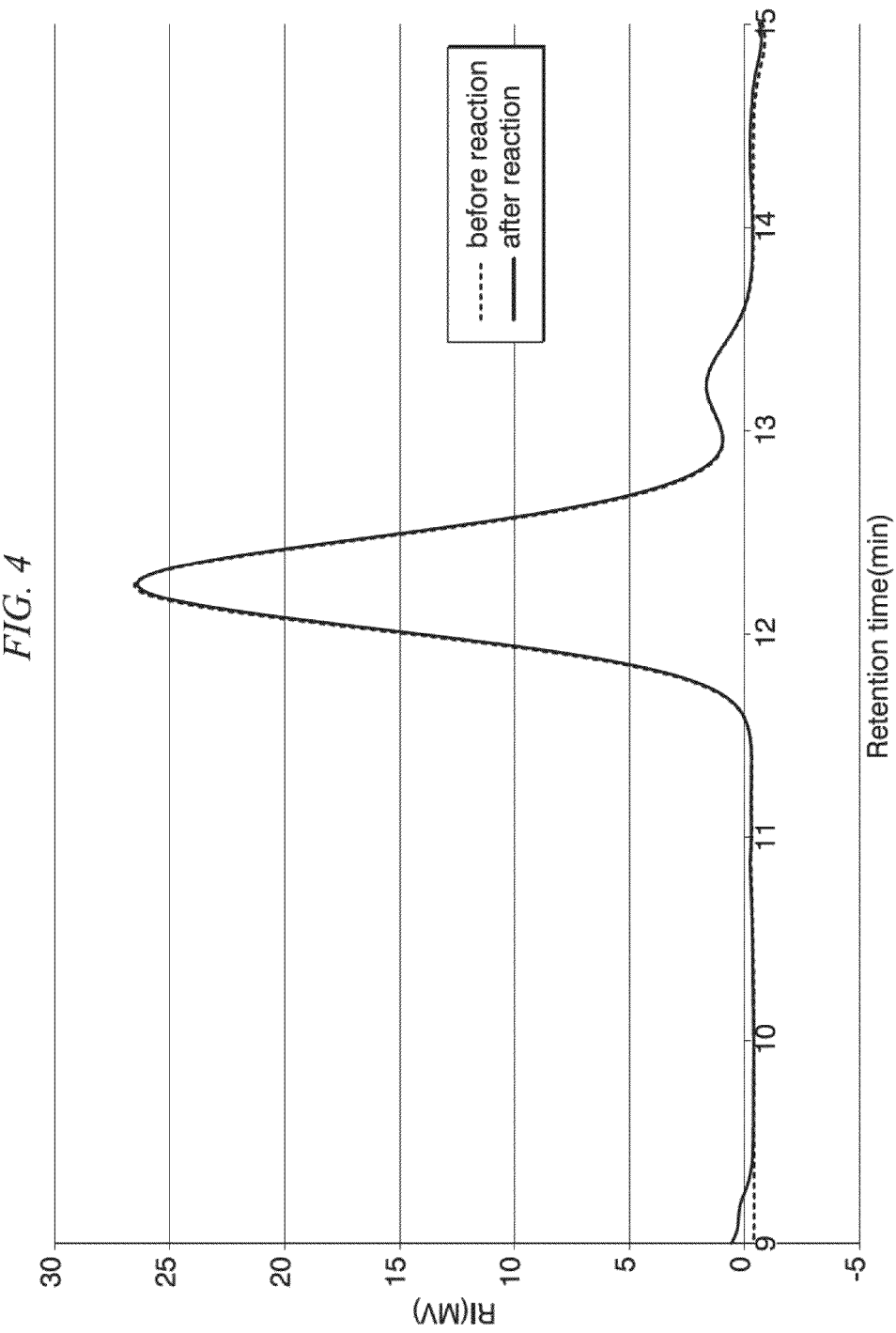
FIG. 4 is a chart indicating fractions obtained at retention times of 9 minutes to 15 minutes on an HPLC chromatogram of enzyme reaction liquids before and after an enzyme reaction of BGL using xylobiose as a substrate in Example 1.

FIGS. 3 and 4 indicate fractions obtained at retention times of 9 minutes to 15 minutes, at which disaccharides and monosaccharides are thought to elute, on HPLC chromatograms of hydrolysates obtained from each reaction as detected with an RI detector by HPLC. FIG. 3 indicates the HPLC chart for enzyme reaction liquids using cellobiose as a substrate, while FIG. 4 indicates the HPLC chart for enzyme reaction liquids using xylobiose as a substrate.

As shown in FIG. 3, in the case of using cellobiose as a substrate, if a comparison is made between the hydrolysate when the duration of the enzyme reaction is 0 minutes ("before reaction" in the chart) and the hydrolysate when the duration of the enzyme reaction is 90 minutes ("after reaction" in the chart), the peak for cellobiose observed in the vicinity of a retention time of 11 minutes is smaller for the hydrolysate after the reaction than the hydrolysate before the reaction, while the peak for glucose observed in the vicinity of a retention time of 13.3 minutes is larger, thereby confirming that cellobiose is decomposed to glucose by BGL. The specific activity of cellobiose decomposition activity of BGL was 2.36 U/mg.

On the other hand, as shown in FIG. 4, in the case of using xylobiose as a substrate, since the peak for xylobiose was only observed in the vicinity of a retention time of 12.3 minutes even for the hydrolysate when the duration of the enzyme reaction was 90 minutes ("after reaction" in the chart) in the same manner as the hydrolysate when the duration of the enzyme reaction was 0 minutes ("before reaction" in the chart), xylobiose was confirmed to not be decomposed by BGL.

(7) Temperature Dependency of PNPG Decomposition Activity

The temperature dependency of the PNPG decomposition activity of BGL was investigated using the enzyme sample prepared in the aforementioned section (3).

More specifically, after carrying out enzyme reactions in the same manner as described in <Measurement of PNPG Decomposition Activity> in the aforementioned section (4) with the exception of making the reaction temperature 30° C., 45° C., 60° C., 75° C. or 90° C., 200 µL aliquots of the reaction solutions were sampled from each tube followed by measuring absorbance at 420 nm (A420) and calculating the concentration of PNP in the reaction solution after the enzyme reaction from a predetermined calibration curve.

The results of measuring the PNP concentration of each reaction liquid and the values of relative activity (%) based on a value of 100% for the PNPG decomposition activity of the reaction liquid having the highest PNP concentration are shown in Table 2. As shown in Table 2, although BGL demonstrated an extremely high level of PNPG decomposition activity over a temperature range of 30° C. to 75° C., and demonstrated the highest level of PNPG decomposition activity in the case of having reacted at a temperature of 45° C., relative activity at a temperature of 60° C. was also nearly 100%, and relative activity values at a temperature of 30° C. and 75° C. were also extremely high at greater than 80%. On the other hand, there was hardly any PNPG decomposition activity confirmed at a temperature of 90° C.

TABLE 2

|  | Reaction Temperature (° C.) | | | | |
| --- | --- | --- | --- | --- | --- |
|  | 30 | 45 | 60 | 75 | 90 |
| PNP Concentration (µM) | 209.00 | 256.00 | 253.57 | 240.86 | 10.00 |
| Relative Activity (%) | 81.6 | 100.0 | 99.1 | 94.1 | 3.9 |

(8) pH Dependency of PNPG Decomposition Activity

The pH dependency of the PNPG decomposition activity of BGL was investigated using the enzyme sample prepared in the aforementioned section (3).

More specifically, after carrying out enzyme reactions in the same manner as described in <Measurement of PNPG Decomposition Activity> in the aforementioned section (4) with the exception of using 200 mM HCl—KCl buffer (pH 1.5), citrate-phosphate buffer (pH 3.0), 200 mM acetic acid buffer (pH 3.0), 200 mM acetic acid buffer (pH 5.5) or 200 mM sodium phosphate buffer (pH 8.0) for the buffer mixed with the PNPG solution, 200 µL aliquots of the reaction solutions were sampled from each tube followed by measuring absorbance at 420 nm (A420) and calculating the concentration of PNP in the reaction solution after the enzyme reaction from a predetermined calibration curve.

The results of measuring the PNP concentration of each reaction liquid and the values of relative activity (%) based on a value of 100% for the PNPG decomposition activity of the reaction liquid having the highest PNP concentration are shown in Table 3. In Table 3, "3.0 (A)" indicates the results for the reaction liquid in which citrate-phosphate buffer (pH 3.0) was used, while "3.0 (B)" indicates the results for the reaction liquid in which 200 mM acetic acid buffer (pH 3.0) was used. As shown in Table 3, although BGL demonstrated PNPG decomposition activity at least within the range of pH 3 to pH 5.5 and demonstrated the highest level of PNPG decomposition activity at pH 3.0, it did not demonstrate PNPG decomposition activity at pH 1.5 and demonstrated hardly any PNPG decomposition activity at pH 8.0.

TABLE 3

|  | Reaction Liquid pH | | | | |
| --- | --- | --- | --- | --- | --- |
|  | 1.5 | 3.0(A) | 3.0(B) | 5.5 | 8.0 |
| PNP Concentration (µM) | −0.30 | 221.57 | 203.10 | 209.00 | 3.14 |
| Relative Activity (%) | −0.1 | 100.0 | 91.7 | 94.3 | 1.4 |

INDUSTRIAL APPLICABILITY

The β-glucosidase according to the present invention, a polynucleotide used for the production thereof, an expression vector incorporated with that polynucleotide, and a transformant introduced with that expression vector can be used, for example, in the field of energy production from cellulose-based biomass.

[Accession Number]
FERM BP-11508

---

The invention claimed is:

1. A recombinant β-glucosidase, comprising a β-glucosidase catalytic domain which comprises:
   (A) a polypeptide comprising an amino acid sequence represented by SEQ ID NO. 1,
   (B) a polypeptide comprising an amino acid sequence in which one to 20 amino acids are deleted, substituted, or added in the amino acid sequence represented by SEQ ID NO: 1, and having β-glucosidase activity, or
   (C) a polypeptide comprising an amino acid sequence having 95% or greater sequence identity with the amino acid sequence represented by SEQ ID NO: 1, and having β-glucosidase activity.

2. The β-glucosidase according to claim 1, which has β-glucosidase activity at pH 3.0 to pH 5.5 and a temperature of 30° C. to 75° C. that uses p-Nitrophenyl β-D-glucopyranoside as a substrate.

3. A cellulase mixture, comprising the β-glucosidase according to claim 1, and at least one type of other cellulases.

4. A cellulase mixture, comprising the β-glucosidase according to claim 2, and at least one type of other cellulases.

5. A cellulase mixture, comprising a β-glucosidase produced by the method for producing a β-glucosidase and at least one type of other cellulases, wherein
   the method for producing a β-glucosidase comprises generating a polypeptide having β-glucosidase activity in a transformant which is introduced with an expression vector,
   the expression vector is incorporated with a polynucleotide and is able to express the polypeptide having β-glucosidase activity in a host cell, and
   the polynucleotide comprises a region that encodes a β-glucosidase and comprises:
   (a) a base sequence that encodes a polypeptide comprising an amino acid sequence represented by SEQ ID NO: 1,
   (b) a base sequence that encodes a polypeptide comprising an amino acid sequence in which 1 to 20 amino acids are deleted, substituted, or added in the amino acid sequence represented by SEQ ID NO: 1, and having β-glucosidase activity,
   (c) a base sequence that encodes a polypeptide comprising an amino acid sequence having 95% or greater sequence identity with the amino acid sequence represented by SEQ ID NO: 1, and having β-glucosidase activity, or
   (d) a base sequence of a polynucleotide which hybridizes with a polynucleotide comprising the base sequence represented by SEQ ID NO: 2 in a hybridization buffer comprising 6×SSC at 65° C., and being a base sequence that encodes a polypeptide having β-glucosidase activity.

6. A cellulase mixture, comprising a β-glucosidase produced by the method for producing a β-glucosidase according to claim 5, wherein said transformant is a eukaryotic microbe and at least one type of other cellulases.

7. A cellulase mixture, comprising a β-glucosidase produced by the method for producing a β-glucosidase according to claim 5, wherein said transformant is a filamentous fungus and at least one type of other cellulases.

* * * * *

```
                        SEQUENCE LISTING

<160> NUMBER OF SEQ ID NOS: 12

<210> SEQ ID NO 1
<211> LENGTH: 619
<212> TYPE: PRT
<213> ORGANISM: Acremonium cellulolyticus

<400> SEQUENCE: 1

Met Lys Ser Leu Ser Leu Leu Ala Ala Ala Val Ala Val Val Gln Ala
1               5                   10                  15

Gln Glu Val Tyr Ile Thr Thr Ser Gly Tyr Thr Ala Arg Pro Gln Cys
            20                  25                  30

Thr Glu Pro Pro Ala Thr Pro Thr Tyr Arg Phe Gln Ser Phe Ser Tyr
        35                  40                  45

Ala Ser Leu Asn Asp Thr Val Arg Tyr Ala Ile Ser Val Pro Ser Pro
    50                  55                  60

Thr Thr Thr His Thr Tyr Gly Pro Ala Tyr Ser Glu Ala Val Ala Lys
65                  70                  75                  80

Leu Ser Thr Thr Leu Ser Thr Thr Thr Trp Gly Ser Trp Leu Pro Gly
                85                  90                  95

Gln Thr Ile Ile Ser Ala Thr Asp Thr Ala Asp Lys Tyr Gly Gln Ala
            100                 105                 110

Ala Trp Ser Ser Gln Trp Leu His Ala Ser Leu Ala Asn Tyr Thr Asp
        115                 120                 125

Ile Gly Leu Tyr Thr Thr Thr Val Ser Pro Thr Pro Leu Pro Thr Ser
    130                 135                 140

Glu Leu Val Leu Pro Pro Arg Asp Tyr Phe Gly Pro Thr Asp Cys Tyr
145                 150                 155                 160

Asn Phe Pro Glu Gly Phe Thr Phe Gly Val Ala Gly Ser Ala Ala Gln
                165                 170                 175

Ile Glu Gly Ala Ile Gly Leu Glu Gly Arg Ala Pro Ser Ile Leu Glu
            180                 185                 190

Lys Met Leu Pro Asp Thr Lys Pro Gln Asp Tyr Val Thr Asn Glu Asn
        195                 200                 205

Tyr Tyr Leu Tyr Lys Gln Asp Ile Gln Arg Leu Ala Ser Ile Gly Val
    210                 215                 220

Lys Tyr Tyr Ser Phe Ser Ile Ser Trp Gly Arg Ile Leu Pro Phe Thr
225                 230                 235                 240

Val Pro Gly Ser Pro Val Asn Glu Gln Gly Ile Lys His Tyr Asn Asp
                245                 250                 255

Leu Ile Asp Tyr Val Leu Glu Val Gly Met Val Pro Ile Val Thr Met
            260                 265                 270

Leu His Phe Asp Thr Pro Leu Tyr Phe Ile Asn Ala Ser Ala Gly Tyr
        275                 280                 285

Ala Val Pro Asp Ile Gly Tyr Gln Asn Gly Gly Tyr Trp Ser Glu Glu
    290                 295                 300

Phe Val Glu Ser Phe Val Asn Tyr Gly Lys Ile Leu Phe Thr His Phe
305                 310                 315                 320

Ala Asp Arg Val Pro Phe Trp Val Thr Ile Asn Glu Pro Leu Leu Tyr
                325                 330                 335
```

Ala Phe Asn Phe Thr Gly Leu Asp Asn Val Val His Ala His Ala Glu
              340                 345                 350

Leu Tyr His Phe Tyr His Asp Thr Leu Asn Gly Thr Gly Lys Val Gly
              355                 360                 365

Leu Lys Leu Asn Asp Asn Phe Gly Val Pro Lys Asn Pro Glu Asn Gln
              370                 375                 380

Thr Glu Ile Asp Ala Ala Asn Arg Phe Asn Asp Met Gln Leu Gly Val
385                 390                 395                 400

Phe Thr Tyr Pro Ile Cys Leu Gly Gln Gln Tyr Pro Lys Ser Ile Leu
              405                 410                 415

Asp Thr Leu Pro Gly Ala Lys Pro Leu Ser Lys Glu Leu Glu Tyr
              420                 425                 430

Ile Ser His Thr Thr Asp Phe Ile Gly Ile Asp Ala Tyr Thr Ala Thr
              435                 440                 445

Val Ile Ser Val Pro Ala Glu Gly Ile Glu Asn Cys Ala Lys Gln Asn
          450                 455                 460

Met Thr Thr Asn Ser Leu Tyr Pro Tyr Cys Val Thr Gln Glu Thr Val
465                 470                 475                 480

Asn Ala Tyr Gly Trp Asp Ile Gly Tyr Arg Ser Gln Ser Tyr Val Tyr
              485                 490                 495

Ile Thr Pro Ile Tyr Leu Arg Thr Tyr Leu Ser Tyr Leu Trp Asn Thr
              500                 505                 510

Tyr Lys Thr Pro Leu Ile Leu Ser Glu Phe Gly Phe Pro Val Tyr Ala
              515                 520                 525

Glu Ser Thr Arg Asp Leu Val Asp Gln Leu Tyr Asp Ser Pro Arg Ser
530                 535                 540

Glu Tyr Tyr Leu Ser Phe Met Ser Glu Val Leu Lys Ser Ile Trp Glu
545                 550                 555                 560

Asp Gly Val Asn Val Ile Gly Ala Ile Ala Trp Ser Phe Met Asp Asn
                  565                 570                 575

Trp Glu Phe Gly Asp Tyr Ala Gln Gln Phe Gly Met Gln Val Val Asn
              580                 585                 590

Arg Thr Thr Gln Glu Arg Trp Phe Lys Lys Ser Phe Phe Asp Ile Val
              595                 600                 605

Asp Phe Val Gly Ala Arg Asn Gly Leu Gly Tyr
          610                 615

<210> SEQ ID NO 2
<211> LENGTH: 1860
<212> TYPE: DNA
<213> ORGANISM: Acremonium cellulolyticus

<400> SEQUENCE: 2
atgaagtccc tctctctact agcagcggcc gttgctgtag tacaagccca agaagtgtac      60
attacgactt ctggctacac agcgcgacca caatgcactg aacctccggc tacgccaacc     120
taccgcttcc agtcgttctc atatgcatcg ctcaatgaca ctgttagata tgccatctca     180
gtcccttccc caacgactac ccacacctat ggaccagcat actccgaagc agtagcaaaa     240
ttatcaacga ccctctcaac tacgacatgg ggtagttggc taccaggtca gaccatcatt     300
tctgcaacgg acacggccga caaatacggt caagccgcgt ggtcatcgca atggctacat     360
gcaagtttgg caaattatac cgatattggt ttgtacacca ctaccgtcag tcctacgcca     420
ctgcctacta gtgaacttgt ccttccacca cgggactact ttggtccaac cgattgctat     480

```
aactttcctg agggattcac gtttggtgtt gccggatctg ctgctcagat cgaaggtgcc    540
attgggcttg aaggtcgtgc gccgagtata cttgaaaaga tgttgccaga tacaaagccg    600
caggattacg tgactaatga aactattac ctgtataagc aggacattca gcgcttggca    660
tcgattggcg tcaagtatta cagtttctcg atctcgtggg gccgtattct accgtttaca    720
gtacccggaa gtcctgttaa tgaacaaggc atcaagcatt acaacgatct gattgactat    780
gttctggagg tcgggatggt gccaattgtg acgatgcttc atttcgatac tccattgtat    840
ttcatcaatg cgtctgctgg ttacgcagtg ccggatattg ataccagaa tgggggttac    900 tggagtgaag aatttgtcga gtcatttgtg aactacggca agattctctt tacgcatttt    960
gcggaccgtg ttccgttctg ggtcacgatt aatgagcctc tgctgtatgc gtttaatttt   1020
acgggactgg acaatgttgt gcatgctcat gcggagttgt atcatttcta tcatgatacc   1080
ttgaatggaa ctggcaaagt gggattgaag ttgaatgata actttggcgt gcctaagaac   1140
cccgagaatc agaccgaaat cgatgccgcc aaccgtttca atgacatgca gctcggcgtc   1200
tttacatatc cgatttgtct cggacagcaa tatcccaaat ccatcctcga tactcttcca   1260
ggtgccaagc cactcagcaa aaaagaattg gaatatatca gccataccac cgacttcatc   1320
ggcatcgacg cctacacagc caccgtcatc tcggtccctg ccgaaggcat cgaaaactgc   1380
gccaaacaga acatgaccac caattcgttg tatccctact gtgtcactca agaaaccgta   1440
aacgcatatg gctgggacat cggctaccgc tcccaatcct acgtctacat cacacccatc   1500
tacctccgga catacctttc ttatctctgg aacacctaca aaaccccgct catcctcagc   1560
gaattcgggt ttcccgtgta cgcagaatca acgcgcgatc tagtcgacca actgtacgac   1620 tcccccgaa gtgaatatta tttatcgttt atgtctgagg tactcaaatc gatatgggaa   1680
gacggagtaa atgtgattgg ggcgattgcg tggagtttta tggataattg ggagtttggg   1740
gattatgcgc agcagtttgg gatgcaggtt gtcaatcgga cgacgcagga gaggtggttt   1800
aagaagagtt tctttgacat tgtggatttt gtgggagcga ggaatgggtt gggttattga   1860
```

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Primer.

<400> SEQUENCE: 3

```
tcctccaagt tacccatgaa gtccctctct                                      30
```

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Primer.

<400> SEQUENCE: 4

```
cgcttcgtcg acccctcaat aacccaaccc                                      30
```

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Primer.

<400> SEQUENCE: 5

-continued

```
atgctcggga gctttggatt tcctacgtct tc                                32
```

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Primer.

<400> SEQUENCE: 6

```
atgcatatgt cgagagtgtt gtgtgggtca acg                               33
```

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Primer.

<400> SEQUENCE: 7

```
atggtcgacg aagcgtaaca ggatagccta gac                               33
```

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Primer.

<400> SEQUENCE: 8

```
atgcccgaga gtaacccatt cccggttctc tag                               33
```

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Primer.

<400> SEQUENCE: 9

```
atggctagca gatctcgcgg cagggttgac                                   30
```

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Primer.

<400> SEQUENCE: 10

```
atggtcgacc ccgggtaact tggaggacgg aagaaaagag                        40
```

<210> SEQ ID NO 11
<211> LENGTH: 529
<212> TYPE: PRT
<213> ORGANISM: Acremonium cellulolyticus
<220> FEATURE:
<223> OTHER INFORMATION: Cellobiohydrolase1

<400> SEQUENCE: 11

Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

-continued

```
Ala Glu Thr His Pro Ser Leu Ser Trp Ser Thr Cys Lys Ser Gly Gly
         35                  40                  45

Ser Cys Thr Thr Asn Ser Gly Ala Ile Thr Leu Asp Ala Asn Trp Arg
 50                  55                  60

Trp Val His Gly Val Asn Thr Ser Thr Asn Cys Tyr Thr Gly Asn Thr
 65                  70                  75                  80

Trp Asn Ser Ala Ile Cys Asp Thr Asp Ala Ser Cys Ala Gln Asp Cys
                 85                  90                  95

Ala Leu Asp Gly Ala Asp Tyr Ser Gly Thr Tyr Gly Ile Thr Thr Ser
                100                 105                 110

Gly Asn Ser Leu Arg Leu Asn Phe Val Thr Gly Ser Asn Val Gly Ser
            115                 120                 125

Arg Thr Tyr Leu Met Ala Asp Asn Thr His Tyr Gln Ile Phe Asp Leu
        130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
                180                 185                 190

Tyr Cys Asp Ser Gln Cys Pro Arg Asp Leu Lys Phe Ile Ala Gly Gln
            195                 200                 205

Ala Asn Val Glu Gly Trp Thr Pro Ser Ser Asn Asn Ala Asn Thr Gly
        210                 215                 220

Ile Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
                260                 265                 270

Arg Tyr Ala Gly Thr Cys Asp Pro Asp Gly Cys Asp Phe Asn Pro Tyr
            275                 280                 285

Arg Leu Gly Val Thr Asp Phe Tyr Gly Ser Gly Lys Thr Val Asp Thr
        290                 295                 300

Thr Lys Pro Phe Thr Val Val Thr Gln Phe Val Thr Asn Asp Gly Thr
305                 310                 315                 320

Ser Thr Gly Ser Leu Ser Glu Ile Arg Arg Tyr Tyr Val Gln Asn Gly
                325                 330                 335

Val Val Ile Pro Gln Pro Ser Ser Lys Ile Ser Gly Ile Ser Gly Asn
            340                 345                 350

Val Ile Asn Ser Asp Tyr Cys Ala Ala Glu Ile Ser Thr Phe Gly Gly
        355                 360                 365

Thr Ala Ser Phe Ser Lys His Gly Gly Leu Thr Asn Met Ala Ala Gly
    370                 375                 380

Met Glu Ala Gly Met Val Leu Val Met Ser Leu Trp Asp Asp Tyr Ala
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Thr Cys Ala Thr Thr Ser Gly Asp Pro
            420                 425                 430

Lys Thr Val Glu Ala Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
```

```
              450                 455                 460
Gly Gly Ser Thr Thr Thr Ala Ser Arg Thr Thr Thr Ser Ala
465                 470                 475                 480

Ser Ser Thr Ser Thr Ser Ser Thr Gly Thr Gly Val Ala Gly
                485                 490                 495

His Trp Gly Gln Cys Gly Gly Gln Gly Trp Thr Gly Pro Thr Thr Cys
                500                 505                 510

Val Ser Gly Thr Thr Cys Thr Val Val Asn Pro Tyr Tyr Ser Gln Cys
                515                 520                 525

Leu

<210> SEQ ID NO 12
<211> LENGTH: 226
<212> TYPE: PRT
<213> ORGANISM: Acremonium cellulolyticus
<220> FEATURE:
<223> OTHER INFORMATION: Endoglucanase

<400> SEQUENCE: 12

Met Lys Leu Thr Phe Leu Leu Asn Leu Ala Val Ala Ala Ser Ala Gln
1               5                   10                  15

Gln Ser Leu Cys Ser Gln Tyr Ser Ser Tyr Thr Ser Gly Gln Tyr Ser
                20                  25                  30

Val Asn Asn Asn Leu Trp Gly Glu Ser Ser Gly Ser Gly Ser Gln Cys
                35                  40                  45

Thr Tyr Val Asn Ser Ile Ser Ser Ser Gly Val Ser Trp Ser Thr Thr
        50                  55                  60

Trp Asn Trp Ser Gly Gly Ser Thr Ser Val Lys Ser Tyr Ala Asn Ser
65                  70                  75                  80

Gln Leu Ser Gly Leu Thr Lys Lys Leu Val Ser Asn Leu Gln Ser Ile
                85                  90                  95

Pro Thr Ser Val Gln Trp Ser Tyr Ser Asn Thr Asn Ile Val Ala Asp
                100                 105                 110

Val Ser Tyr Asp Leu Phe Thr Ala Ala Asp Ile Asn His Val Thr Tyr
                115                 120                 125

Ser Gly Asp Tyr Glu Leu Met Ile Trp Leu Gly Lys Tyr Gly Gly Ala
                130                 135                 140

Gln Pro Leu Gly Ser Gln Ile Gly Thr Ala Asn Val Gly Gly Ala Thr
145                 150                 155                 160

Trp Gln Leu Trp Tyr Gly Val Asn Gly Ser Gln Lys Thr Tyr Ser Phe
                165                 170                 175

Val Ala Ser Ser Gln Thr Thr Ser Trp Asn Gly Asp Ile Leu Gln Phe
                180                 185                 190

Phe Lys Tyr Leu Gln Ser Asn Gln Gly Phe Pro Ala Ser Ser Gln Tyr
                195                 200                 205

Leu Ile Asp Leu Gln Phe Gly Thr Glu Pro Phe Thr Gly Ser Gln Thr
                210                 215                 220

Thr Leu
225
```